United States Patent [19]

Borowski et al.

[11] Patent Number: 5,942,495
[45] Date of Patent: Aug. 24, 1999

[54] ANTIBIOTICS

[75] Inventors: Edward Borowski; Jolanta Grzybowska, both of Gdansk; Pawel Sowinski, Sopot, all of Poland; Jerzy Gumieniak; Andrzej Czerwinski, both of Stafford, Tex.

[73] Assignee: BTG International Limited, London, United Kingdom

[21] Appl. No.: 08/857,281

[22] Filed: May 16, 1997

Related U.S. Application Data

[63] Continuation-in-part of application No. PCT/GB96/01144, May 10, 1996, abandoned
[60] Provisional application No. 60/020,464, May 17, 1996.

[51] Int. Cl.$^6$ .............................. A61K 32/70; C07H 17/08
[52] U.S. Cl. .............................................. 514/31; 536/6.5
[58] Field of Search .................................. 536/6.1; 514/31

[56] References Cited

U.S. PATENT DOCUMENTS

| | | | |
|---|---|---|---|
| 4,002,741 | 1/1977 | Kulbakh et al. | 514/31 |
| 4,093,796 | 6/1978 | Falkowski et al. | 536/6.5 |
| 4,144,328 | 3/1979 | Vainshtein et al. | 514/31 |
| 4,195,172 | 3/1980 | Falkowski et al. | 536/6.5 |
| 5,314,999 | 5/1994 | Seman et al. | 536/6.5 |

FOREIGN PATENT DOCUMENTS 0 394 938 A2  10/1990  European Pat. Off. .

OTHER PUBLICATIONS

Abstract of JP93059084, 1 page, Nov. 23, 1993.
DN&P 10(10), p. 617, Dec. 1997.
Falkowski et al "N–Glycosyl Derivatives of Polyene Macrolide Antibiotics" J. Antibiotics, vol. XXVIII, N° 3 (1975) pp. 244–245.
Corbett et al "Synthesis and Antifungal Activity of C–16 Oximino and Vinyl Amphotericin B Derivatives" J. Antiobiotics, vol. 48, N° 6 (1995) pp. 509–515.
Borowski et al "2$^{nd}$ Generation Amphotencin B Derivatives of Low Toxicity: Design & Properties" 95$^{th}$ General Meeting of American Society for Microbiology Washington (Abstracts) (1995), Abstract F–107.
Cheron et al "Quantitative Structure–Activity Relationships in Amphortericin B Derivities" Biochemical Pharmacology, vol. 37, N° 5 (1988) pp. 827–836.
Falkowski et al "The Structure of N–Glycosyl Derivatives of Polyene Macrolide Antibiotics, the Reaction of Nystatin with D–Glucose", Polish Journal of Chemistry vol. 56 (1982) pp. 123–130.
Czerwinski et al "N–Dimethylaminoacyl Derivatives of Polyene Macrolide Antibiotics" J. Antibiotics, vol. XXXIX N° 7 pp. 1025–1027.
Wright et al "N–Aminoacyl Derivatives of Polyene Macrolide Antibiotics and their Esters", J. Antibiotics, vol. XXXV N° 7 (1982) pp. 911–914.

Pleskoff et al, "Amphotericin B Derivative Blocks Human Immunodeficiency Virus Type 1 Entry after CD4 Binding: Effect on Virus–Cell Fusion but Not on Cell–Cell Fusion", J. Virology vol. 69 N° 1 (1995) pp. 570–574.
Céfai et al "MS–8209, A New Amphotericin B Derivative that Inhibits HIV–1 Replication in vitro and Restores T–Cell Activation via the CD3/TcR in HIV–infected CD4+ Cells" AIDS vol. 5 N° 12 (1991) pp. 1453–1461.
Saint–Julien et al "Activity of MS–8209, a Nonester Amphotericin B Derivative, in Treatment of Experimental Systemic Mycoses" Antimicrobial Agents and Chemotherapy, vol. 36 N° 12 (1992) pp. 2722–2728.

*Primary Examiner*—Elli Peselev
*Attorney, Agent, or Firm*—Nixon & Vanderhye

[57] ABSTRACT

The invention relates to an N-alkyl-N-glycosyl derivative of antifungal antibiotics of the polyene macrolide group of general formula 1(a), wherein M represents polyene macrolide antibiotics residues, R represents a variable part of sugar residue, $R^1$ represents a $C_{1-4}$ alkyl group and $R^2$ represents hydrogen or a $C_{1-4}$ alkyl group; their salts of general formula 2(a), wherein R, $R^1$, $R^2$ and M are as herein defined and A represents an anion of organic or inorganic acid. Compounds of formula 1(b) and 2(b) wherein the N-alkyl and alkyl ester groups are represented by methyl are of particular interest.

The invention relates also to processes for preparation of the compounds, to compositions containing these compounds and to their use in therapy and the treatment of external and internal fungal infections in humans and animals.

Formula 1a $$\begin{array}{c} M - COOR^2 \\ | \\ R^1 - N - CH \underset{HO}{\overset{O}{\underset{C}{\diagdown}}} \\ \phantom{R^1 - N - CH\ HO}R \end{array}$$

Formula 1b $$\begin{array}{c} M - COOCH_3 \\ | \\ H_3C - N - CH_2 \underset{HO}{\overset{O}{\underset{C}{\diagdown}}} \\ \phantom{H_3C - N - CH_2\ HO}R \end{array}$$

Formula 2a $$\left[\begin{array}{c} M - COOR^2 \\ | \\ R^1 - N - CH_2 \underset{HO}{\overset{O}{\underset{C}{\diagdown}}} \\ | \\ H \phantom{\ HO}R \end{array}\right]^{\oplus} A^{\ominus}$$

Formula 2b $$\left[\begin{array}{c} M - COOCH_3 \\ | \\ H_3C - N - CH_2 \underset{HO}{\overset{O}{\underset{C}{\diagdown}}} \\ | \\ H \phantom{\ HO}R \end{array}\right]^{\oplus} A^{\ominus}$$

39 Claims, No Drawings

ANTIBIOTICS

This application claims benefit of Provisional Application Ser. No. 60/020,464 filed May 17, 1996. This application is a continuation-in-part of PCT/GB96/01144, filed May 10, 1996, now abandoned.

The invention relates to N-alkyl-N-glycosyl derivatives of antifungal antibiotics of the polyene macrolide group of general formula 1(a), wherein M represents polyene macrolide antibiotics residues, R represents a variable part of sugar residue, $R^1$ represents a $C_{1-4}$ alkyl group and $R^2$ represents hydrogen or a $C_{1-4}$ alkyl group; to salts of compound 1(a), represented by the general formula 2(a), wherein M, R, $R^1$, $R^2$ are as defined above and A represents an anion of an inorganic or organic acid; to methods of preparation of compounds of general formula 1(a) and 2(a) and their use in medicine.

Compounds of particular interest include N-methyl-N-glycosyl derivatives of methyl esters of antifungal antibiotics of polyene macrolide group of general formula 1(b), wherein M represents polyene macrolide antibiotics residues, wherein R represents a variable part of sugar residue, and their salts of general formula 2(b), wherein M represents polyene macrolide antibiotics residues, wherein R represents a variable part of sugar residue, and A represents an anion of inorganic or organic acid, and to methods of their preparation, and use in medicine.

N-alkyl derivatives of antibiotics of polyene macrolide group wherein the amino group of the parent antibiotic is substituted by an alkyl group are known.

N-glycosyl derivatives of polyene macrolides wherein amino group of the parent antibiotic is substituted with a residue of sugar are also known (J. Antibiotics 28, 244 (1975), L. Falkowski, J. Golik, P. Kolodzicjczyk, J. Pawlak, J. Zieliński, T. Zimiński, E. Borowski; Acta Polon. Pharm. 37, 517 (1980), L. Falkowski, J. Pawlak, J. Golik, P. Kolodziejczyk, B. Stefańska, E. Bylec, E. Borowski). Examples of sugars used in the preparation of these derivatives include D-glucose, D-mannose, L-rhanmose, D-ribose and maltose. Upon reaction of polyene macrolides with the appropriate sugar a simultaneous Amadori rearrangement occurs to give the corresponding N-glycosyl derivatives. The compounds have the advantage that they exhibit a biological activity similar to those of the starting antibiotics and form water soluble salts. However, the high toxicity associated therewith represents a significant disadvantage.

From papers J. Antibiotics 28, 244 (1975), L. Falkowski, J. Golik, P. Kolodziejczyk, J. Pawlak, J. Zieliński, T. Zimiński, E. Borowski; Acta Polon. Pharm. 37, 517 (1980), L. Falkowski, J. Pawlak, J. Golik, P. Kolodziejczyk, B. Stefańska, E. Bylec, E. Borowski), there are known N-glycosyl derivatives of polyene macrolides, in which the amino group of the parent antibiotic is substituted with a residue of sugar, such as a D-glucose, D-mannose, L-rhamnose, D-ribose, maltose. The compounds are prepared by reaction of polyene macrolides with the listed sugars, and simultaneous Amadori rearrangement. The compounds exhibit the biological activity similar to those of the starting antibiotics and form water soluble salts. However, they exhibit high toxicity.

Trimethylammonium derivatives of polyene macrolides methyl esters wherein the amino group of the parent antibiotic is fully methylated to give a quaternary ammonium salt are also known (J. Antibiotics 32, 1080 (1979), L. Falkowski, B. Stafańska, J. Zieliński. E. Bylec, J. Golik, P. Kolodziejczyk, E. Borowski). The compounds are prepared by exhaustive methylation of the parent antibiotic with dimethyl sulphate. Advantageous properties of the derivatives include their solubility in water and an antifungal activity similar to that of the starting antibiotics. Unfortunately they are very toxic and unstable.

Anther type of derivatives are trimethylammonium derivatives of polyene macrolides methyl esters, which are known from a paper—J. Antibiotics 32, 1080 (1979), L. Falkowski, B. Stefańska, J. Zieliński, E. Bylec, J. Golik, P. Kolodziejczyk, E. Borowski and in these compounds the amino group of the antibiotic methyl esters is fully methylated to give quaternary ammonium salt. The compounds are prepared by exhaustive methylation of the parent antibiotic with dimethyl sulphate. The derivatives are soluble in water and are characterized by antifungal activity similar to the activity of the starting antibiotics, but they are very toxic and unstable.

Other types of N-alkyl derivatives include the N-succinimidyl derivatives formed by Michael addition reaction of the antibiotics and N-substituted maleimides, such as N-ethylmaleimide, N,N'-hexamethylenedimaleimide, N-(3-dimethylaminopropyl) maleimide; the compounds are known from a paper—J. Antibiotics, 44, 979 (1991), A. Czerwiński, W. A. König, T. Zieniawa, P. Sowiński, V. Sinnwell, S. Milewski, E. Boroski. Such cop-outs are less toxic than the parent antibiotics, but their antifungal activity is diminished.

Finally, the last known group of N-alkyl derivatives of polyene macrolides are N-enamine and amidine derivatives, formed by reaction of the antibiotics with acetylacetone, ethyl acetylacetate, dimethylacetal or dimethylformamide, the compounds are presented in a paper—Acta Polonica Phann. 45, 71 (1988). B. Stefańiska, J. Zieliński, E. Borowski, T. Falkowski. The derivatives exhibit antifungal activity similar to those of the parent antibiotics and improved solubility in organic solvents, however, they are still significantly toxic and very unstable.

The present inventors have now prepared mixed N-alkyl-N-glycosyl derivatives of alkyl esters of polyene macrolide antibiotics as well as the free acid. Methods of preparation of these mixed compounds have also been established. These novel compounds have been found to have high anti-fungal activity, similar to those of the parent antibiotics, form water soluble salts with acids; and are significantly less toxic. These properties are unexpected since all of the N-alkyl derivatives of polyene macrolides of the prior art exhibit a high toxicity, which is a considerable disadvantage. The compounds comprised by the invention are devoid of this disadvantage.

Until now, N-methyl-N-glycosyl derivatives of methyl esters of polyene macrolide antibiotics and methods of their preparation were unknown. Surprisingly, such compounds preserve high antifungal activity, similar to those of the parent antibiotics, they form water soluble salts with acids, and are dramatically less toxic. These compounds do not exhibit the same toxicity as the N-alkyl derivatives of the prior art. A high toxicity constitutes the basic drawback of all known before N-alkyl derivatives of polyene macrolides, and the compounds comprised by the invention are devoid of this disadvantage.

A first aspect of the invention provides an N-alkyl-N-glycosyl derivative of antibiotics of the polyene macrolide group of general formula 1(a), wherein M represents residue of an antibiotic of polyene macrolide group, R represents a part of sugar residue formed by reaction of the antibiotic with a mono or oligosaccharide, $R^1$ represents a $C_{1-4}$ alkyl group and $R^2$ represents hydrogen or a $C_{1-4}$ alkyl group.

Formula 1(a)

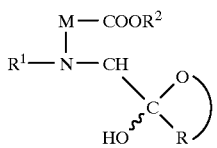

Preferably the residue of the antibiotic of polyene macrolide group M is selected from amphotericin B, candidin, candidoin, candidinin, mycoheptin, nystatin, pollyfungin, aurcofacin, vacidin, trichomycin or candicidin.

It is preferred that the mono or oligosaccharide from which the sugar residue R is derived is selected from D-glucose, or L-glucose, or D-mannose, or D-galactose, or lactose, or maltose. Upon reaction of polyene macrolides with the appropriate sugar a simultaneous Amadori rearrangement occurs to give the N-glycosyl precursors to the compounds of the invention.

A preferred embodiment of the first aspect of the invention comprises an N-methyl-N-glycosyl derivative of a methyl ester of antibiotics of the polyene macrolide group presented by general formula 1(b), wherein M represents residue of an antibiotic of polyene macrolide group, wherein R represents a part of sugar residue formed by reaction of the antibiotic with mono or oligosaccharide, preferably with D-glucose, or L-glucose, or D-mannose, or D-galactose, or lactose, or maltose, and by simultaneous Amadori rearrangement.

Formula 1(b)

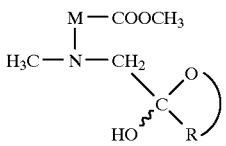

The invention in its preferred form relates to the derivatives wherein the antibiotic of polyene macrolide group is amphotericin B, or candidin, or candidoin, or candidinin, or mycoheptin, or nystatin, or polyfungin, or aureofacin, or vacidin, or trichomycin or candicidin.

A second aspect of the invention provides a salt of an N-alkyl-N-glycosyl derivative of antibiotics of the polyene macrolide group of general formula 2(a) wherein M, R, $R^1$ and $R^2$ are as defined above for the first aspect of the invention and A represents an anion of an organic or inorganic acid. It is preferred that the salt is a physiologically acceptable salt and compounds wherein A is the anion of L-aspartic acid are especially preferred. Salts wherein $R_1$ and $R_2$ are methyl groups are especially preferred.

Formula 2(a)

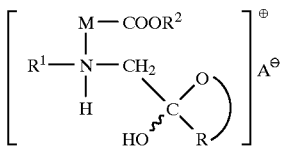

A preferred embodiment of the second aspect of the invention comprises a salt of an N-methyl-N-glycosyl derivative of antibiotics of the polyene macrolide group presented by general formula 2(b) wherein M represents residue of an antibiotic of polyene macrolide group, wherein R represents a part of sugar residue formed by reaction of the antibiotic with mono or oligosaccharide, preferably with D-glucose, or L-glucose, or D-mannose, or D-galactose, or lactose, or maltose, and by simultaneous Amadori rearrangement, and A represents an anion of organic or inorganic acid.

Formula 2(b)

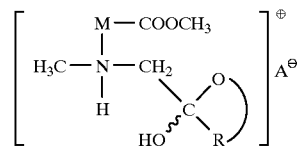

The invention in its preferred form relates to the salts wherein the antibiotic of polyene macrolide group is amphotericin B, or candidin, or candidoin, or candidinin, or mycoheptin, or nystatin, or polyfungin, or aureofacin, or vacidin, or trichomycin or candicidin, and also preferably A relates to the anion of L-aspartic acid.

A third aspect of the invention comprises a method of preparation of compounds of formula 1(a) wherein M, R, $R^1$ and $R^2$ are as defined above for the first and second aspects of the invention and which comprises the steps of reacting a polyene macrolide antibiotic with a mono or oligosaccharide, the reaction being characterised by the occurrence of a simultaneous Amadori rearrangement, to give the N-glycosyl derivatives of the polyene macrolide antibiotics; isolating the product of the Amadori rearrangement, treating the product with an alkylating agent and purifying the crude product.

In one embodiment of the third aspect of the invention the product of the Amadori rearrangement is isolated in the form of a suspension by precipitation from the solution in which the rearrangement occurs. Organic solvents such as N,N-dimethylformamide are preferred to support the Amadori rearrangement. Organic solvents such as diethyl ether are suitable to effect formation of a suspension by precipitation of the product of the Amadori rearrangement.

In a second embodiment of the third aspect of the invention alkylation of the product of the Amadori rearrangement is carried out at reduced temperature. Temperatures of between −5° C. and +5° C. are preferred. Alkylating agents such as diazo alkanes may be used. An ethereal solution of diazomethane is the preferred alkylating agent.

Crude N-alkyl-N-glycosyl products can be isolated upon removal of the solvent and precipitation from diethyl ether. The pure product may be isolated using known purification procedures.

A preferred embodiment of the third aspect of the invention comprises a process for preparation of an N-methyl-N-glycosyl derivative of a methyl ester of antibiotics of the polyene macrolide group presented by general formula 1(b), wherein M represents residue of an antibiotic of polyene macrolide group, wherein R represents a part of sugar residue formed by reaction of the antibiotic with a mono or oligosaccharide, preferably with D-glucose, or L-glucose, or D-mannose, or D-galactose, or lactose, or maltose, and by simultaneous Amadori rearrangement, wherein the product obtained by Amadori rearrangement of the N-glycosyl derivative of antibiotics of the polyene macrolide group is transformed into suspension by precipitation with solvent, preferably diethyl ether, from a solution of the derivatives in organic solvent, preferably in N,N-dimethylformamide, and subsequently treated with ethereal solution of diazomethane at lowered temperature, preferably in the range from −5° C.

to +5° C., stirred, and isolated by evaporation of solvents, and precipitation form the concentrated solution, preferably by an excess of diethyl ether, then, the crude product is purified according to known procedures.

A fourth aspect of the present invention provides an alternative method for the preparation compounds of formula 1(a) wherein M, R, $R^1$ and $R^2$ are as defined above for the first and second aspects of the invention and which comprises the steps of reacting a polyene macrolide antibiotic with a species which provides a protecting group to give a first N-protected (amino) derivative; reacting said first N-protected derivative with a further protecting group providing species thereby protecting the carboxy group of the macrolide to give a second N-protected-carboxy-protected derivative; reacting said second derivative with an alkylating agent to give the N-alkyl N-protected-carboxy-protected derivative; removing the N-protecting group and reacting the resulting N-alkyl derivative with a mono, di- or oligosaccharide, the reaction being characterised by the occurrence of a simultaneous rearrangement, to give the N-alkyl-N-glycosyl derivative; removal of the carboxy protecting group from said N-alkyl-N-glycosyl derivative followed by the required derivatisation of said carboxy group.

The choice of amino protecting group will be apparent to those skilled in the art. Species which provide trifluoroacetyl N-protecting groups are of most interest. Typical examples include trifluoroacetic anhydride and trifluoroacetic acid.

The nature of the carboxy protecting groups will also be apparent to a skilled person. Species giving rise to labile ester groups at the carboxy centre are preferred. Typical groups used for protection include benzyl esters, p-methoxybenzyl ester and t-butyl ester.

The choice of alkylating agents will also be apparent to persons skilled in the art. Preferred alkylating agents include the appropriate dialkyl sulphate and alkyl iodides. Dimethyl sulphate and methyl iodide are of particular interest.

Conditions used for removal of the N-protecting group will depend upon the nature of the group itself and will be apparent to a person skilled in the art. Typically the introduction of mildly acidic conditions will suffice. This is particularly the case when N-trifluoroacetyl protecting groups are used.

Similarly, removal of the carboxy protecting group will be likewise depend upon the nature of the protecting group employed. Typical conditions will be apparent to a person skilled in the art.

The introduction of mildly acidic conditions will result in the production of the carboxylic acid where $R^1$ is hydrogen. Reaction of this carboxylic acid form with $C_{1-4}$ alcohols will give the corresponding ester form.

It should therefore be understood that the preparation of mixed N-alkyl-N-glycosyl derivatives wherein $R^1$ and $R^2$ are different is provided by the present invention.

A fifth aspect of the invention provides a method of preparation of a salt of an N-alkyl-N-glycosyl derivative of the polyene macrolide antibiotics of general formula 2(a) wherein M, R, $R^1$ and $R^2$ are as defined above for the first to fourth aspects of the invention and which comprises the steps of suspending an N-alkyl-N-glycosyl derivative prepared according to the third or fourth aspects of the invention in sufficient water to effect formation of a homogeneous suspension, acidifying the resulting suspension and isolating the product. The preparation of salts of N-methyl-N-glycosyl derivatives of methyl esters of polyene macrolide antibiotics is especially preferred.

Organic or inorganic acids may be used to acidify the suspension. L-aspartic acid is preferred.

Isolation of the pure product may be effected by precipitation of the crude product with an organic solvent which is then washed with an additional appropriate solvent and dried. It is preferred that the solvent used to precipitate the crude product is miscible with water; acetone is preferred. Typical solvents employed for washing the product include acetone and diethyl ether. It is preferred that the product is dried under reduced pressure.

A preferred embodiment of the fifth aspect of the invention comprises a process for preparation of salts of N-methyl-N-glycosyl derivatives of methyl esters of antibiotics of polyene macrolide group presented by general formula 2(b), wherein M represents residue of an antibiotic of polyene macrolide group, wherein R represents a part of sugar residue formed by reaction of the antibiotic with mono or oligosaccharide, preferably with D-glucose, or L-glucose, or D-mannose, or D-galactose, or lactose, or maltose, and by simultaneous Amadori rearrangement, wherein the obtained by Amadori rearrangement N-glycosyl derivatives of antibiotics of polyene macrolide group are transformed into suspension by precipitation with solvent, preferably diethyl ether, from a solution of the derivative in organic solvent, preferably in N,N-dimethylformamide, and subsequently treated with ethereal solution of diazomethane at lowered temperature, preferably in the range from −5° C. to +5° C., stirred, and isolated by evaporation of solvents, and precipitation from the concentrated solution, preferably by an excess of diethyl ether, then the crude product is purified according to known procedures, subsequently, the obtained derivative, as a solid, is suspended in small amount of water, and stoichiometric amount of organic or inorganic acid is added, next the product is precipitated from the formed solution by an excess of organic solvent miscible with water, preferably acetone, the solid is then washed, preferably with acetone and subsequently preferably with diethyl ether, and dried, preferably under reduced pressure.

A sixth aspect of the present invention comprises an N-alkyl-N-glycosyl derivative of formula 1(a) or a salt thereof for use in therapy.

A seventh aspect of the invention provides a method for the treatment of fungal infections in humans and animals which comprises the administration thereto of an N-alkyl-N-glycosyl derivative of formula 1(a) or a salt thereof as herein before defined. N-methyl-N-glycosyl derivatives of formula 1(b) or the salts thereof are of particular interest.

A first preferred embodiment of the seventh aspect of the invention comprises a method for treatment of external and internal fungal infections in humans and animals, wherein an N-methyl-N-glycosyl derivative of a methyl ester of antibiotics of the polyene macrolide group presented by general formula 1(b), wherein M represents residue of an antibiotic of polyene macrolide group, wherein R represents a part of sugar residue formed by reaction of the antibiotic with mono or oligosaccharide, preferably with D-glucose, or L-glucose, or D-mannose, or D-galactose, or lactose, or maltose, and by simultaneous Amadori rearrangement are used to treat the infections.

A second preferred embodiment of the seventh aspect of the invention comprises a method for treatment of external and internal fungal infections in humans and animals, wherein salts of N-methyl-N-glycosyl derivatives of methyl esters of antibiotics of polyene macrolide group presented by general formula 2(b), wherein M represents residue of an antibiotic of polyene macrolide group, wherein R represents a part of sugar residue formed by reaction of the antibiotic with mono or oligosaccharide, preferably with D-glucose, or L-glucose, or D-mannose, or D-galactose, or lactose, or maltose, and by simultaneous Amadori rearrangement, and A represents an anion of organic or inorganic acid are used to treat the infections.

An eighth aspect of the invention provides an N-alkyl-N-glycosyl derivative of formula 1(a) or a salt thereof as herein before for use in the treatment of fungal infections. N-methyl-N-glycosyl derivatives of formula 1(b) or the salts thereof are of particular interest.

The infections for which treatment is provided may be internal or external. The mode of administration will depend upon the nature of the infection. Thus the compounds of the invention may be formulated for intravenous, intra peritoneal, oral, topical, subcutaneous, rectal or vaginal administration. For internal infections perfusion of the therapeutic compound is the preferred form of administration. In some instances the use of perfusion in the treatment of external fungal infections will be advantageous.

thereof for the purpose of a medicament for use in the treatment of fungal infections. Compounds wherein the N-alkyl and alkyl ester substituents are both methyl groups are of particular interest.

Structural determinations carried out on the compounds of the invention using spectroscopic methods indicate that the integrity of the parent antibiotic is preserved during the reaction.

The invented process for preparation of N-methyl-N-glycosyl derivatives of methyl esters of antibiotics of polyene macrolide group gives the desired products without changes in structure of the parent antibiotic. Structure of the obtained compounds was proved using spectroscopic methods. The proof is illustrated by determination of the structure of N-methyl-N-D-fructosylamphotericin B methyl ester, of formula 3.

Formula 3

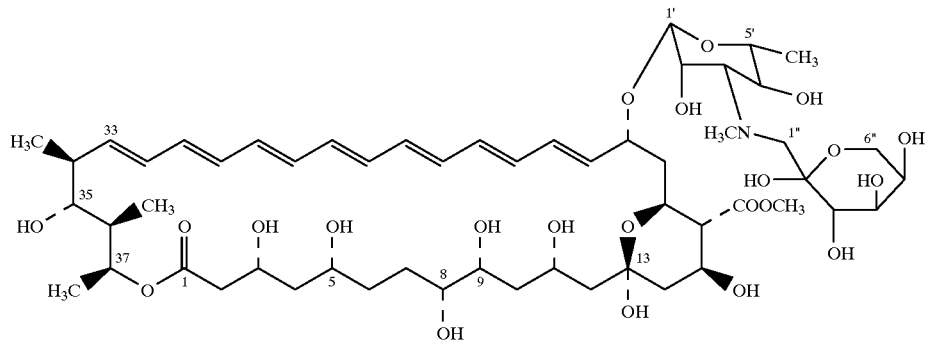

A ninth aspect of the invention provides a method of treatment of fungal infections which comprises the perfusion of compounds of formula 1(a) or salts thereof into the body of a patient suffering therefrom.

A tenth aspect of the invention provides compositions for use in the treatment of fungal infections comprising an N-alkyl-N-glycosyl derivative of formula 1(a) or a salt thereof and a physiologically acceptable carrier. The nature of the N-alkyl-N-glycosyl derivative and the carrier will depend upon the mode of administration. The composition may be formulated from one or more compounds according to the invention, optionally in combination with other known antifungal agents, according to requirements. Compositions containing N-methyl-N-glycosyl derivatives of formula 1(b) or the salts thereof are of particular interest.

An eleventh aspect of the invention provides a unit dosage form comprising one or more N-alkyl-N-glycosyl derivatives of formula 1(a) or salts thereof and a physiologically acceptable carrier formulated for pharmaceutical or veterinary use. The unit dosage form may be formulated from one or more compounds according to the invention optionally in combination with other known antifungal agents. By analogy with the previous aspects of the invention unit dosage forms containing N-methyl-N-glycosyl derivatives of formula 1(b) are of particular interest.

As mentioned above the nature of the unit dosage form will depend upon the mode of administration. Typically tablets and capsules are suitable for oral administration; creams and patches are suitable for topical administration with pessaries being suitable for rectal and vaginal administration.

A twelfth aspect of the invention provides the use of an N-alkyl-N-glycosyl derivative of formula 1(a) or a salt Electronic spectrum of N-methyl-N-D-fructosylamphotericin B methyl ester is identical with that of the parent antibiotic, that means amphotericin B, and demonstrates that the invented method does not lead to degradation of the polyene chromphore, and a high value of extinction ($E^{1\%}_{1\,cm}$=1300 at 382 nm) confirms a high purity of the obtained product. Absorption infrared spectrum of the N-methyl-N-D-fructosylamphotericin B methyl ester demonstrates the band related to stretching vibrations of the ester carbonyl group at 1730 cm$^{-1}$, and lack of band of free carboxylic group, what means that the carboxylic group was completely transformed into methyl ester group. Complete information on structure of the N-methyl-N-D-fructosylamphotericin B methyl ester was provided by nuclear magnetic resonance spectra (NMR) upon $^1$H (DQF-COSY,ROSEY), $^{13}$C(DEPT) and heterocorrelated spectra (Varian 300 MHZ spectrometer) allowed an assignment of the formula 3 for the compound.

The most significant $^1$H and $^{13}$C information are listed in tables 1 and 2, respectively. The NMR data for aglycone of amphotericin B are in full agreement with literature data—Magn.Reson.Chem. 30,275,(1992), P. Sowiński, J. Pawlak, E. Borowski, P. Gariboldi. $^1$H chemical shifts (in DMSO/MeOD solvent system) of N—CH$_3$ ($\delta$=2.35 ppm) and H-1" (2.30 and 3.15 ppm) are characteristic for influence of an amino substituent. After acidification $\delta$ changes to 2.92 ppm for N—CH$_3$, and to 3.64 for H-1" due to the protonation of the amino group ($\delta$ for -3' changes to 3.19 ppm). These data are supported also by ROE effects between protons NCH$_3$/H3', NCH$_3$/H2', NCH$_3$/III"b and 1"a/II3'. Coupling constants and ROE indicate $^4$C$_1$ conformation of the mycosamine moiety, as it was found before for free amphotericin B.

Table 1 presents chemical shifts ¹H and ROE effects of the disaccharide fragment of the N-methyl-N-D-fructosylamphotericin B methyl ester.

TABLE 1

| proton | δ[ppm] pyridine-d$_5$: | ROE for protons methanol-d$_4$ 9:1 | δ[ppm] DMSO-d$_6$: | ROE for protons methanol-d$_4$ 4:6 |
|---|---|---|---|---|
| 1' | 4.77 | 2', 3', 5', 18b, COOMe | 4.48 | 3', 5' |
| 2' | 4.41 | 1', 3', NMc, 17, COOMc, 1"a? | 4.04 | 3', NMe, COOMc |
| 3' | 2.06 | 1', 2', 5', NMC, 1"a, COOMc | 1.89 | 1', 2', NMe, 1"b |
| 4' | 4.38 | 6' | 3.80 | 6' |
| 5' | 3.61 | 1', 3', 6' | 3.45 | 1', 3', 6' |
| 6' | 1.23 | 4', 5' | 1.27 | 4', 5' |
| 1"a | 2.56 | 3', 3" (2') | 2.30 | |
| 1"b | 3.58 | NMe | 3.15 | 3", 3' |
| 3" | 4.41 | 1"a? | 3.65 | 1"b |
| 4" | 4.76 | | 3.97 | |
| 5" | 4.41 | | 3.63 | |
| 6"a | 4.21 | | 3.57 | |
| 6"b | 4.36 | | 3.76 | |
| NMc | 2.29 | 2', 3', 1"b, COOMe | 2.35 | 2', 3', 1"a, 1"b, COOMc |
| COOMe | 3.70 | 1', 2', 3', NMc, 16 | 3.77 | 2', NMe |

Table 2 represents ¹³C-NMR chemical shifts of the disaccharide fragment of the N-methyl-N-D-fructosylamphotericin B methyl ester and their comparison with data for D-fructose.

TABLE 2

| | | data for fructoses* | | |
|---|---|---|---|---|
| carbon | δ[ppm] | β-D-fructopyranose δ[ppm] | α-D-furanose δ[ppm] | β-D-fructofuranose δ[ppm] |
| 1' | 98.2 | | | |
| 2' | 72.4 | | | |
| 3' | 66.4 | | | |
| 4' | 69.8 | | | |
| 5' | 72.3 | | | |
| 6' | 18.2 | | | |
| 1" | 62.2 | 64.1 | 62.1 | 63.9 |
| 2" | 98.1 | 99.1 | 105.3 | 102.4 |
| 3" | 66.9 | 70.5 | 83.0 | 76.5 |
| 4" | 71.2 | 68.4 | 77.0 | 75.5 |
| 5" | 72.2 | 70.0 | 82.2 | 81.5 |
| 6" | 64.6 | 64.7 | 62.1 | 63.3 |
| NMc | 40.9 | | | |
| COOMe | 51.6 | | | |

*S. N. Rosenthal & J. H. Fendler, Progr. Phys. Org. Chem. 13,280 (1976).

Comparison of the ¹³C-NMR data from Table 2 for the fructosyl fragment with literature data for D-fructose indicates the pyranoside form of the sugar substituent. The observed coupling constants, presented in Table 3, evidence a boat conformation of the fructopyranoside ring presented by formula 4. Only this conformation of the ring is in full agreement with the measured coupling constants.

Table 3 presents coupling constants J$_{H,H}$ for protons of the disaccharide fragment of the N-methyl-N-D-fructosylamphotericin B methyl ester (pyridine-d$_5$; methanol-d$_4$9:1), coupling constants and chemical shifts of closely coupled spin system H3"-H6" were refined iteratively by computer simulation.

TABLE 3

| protons | J[Hz] | protons | J[Hz] |
|---|---|---|---|
| 1', 2' | -0 | 1"a, 1"b | 11.6 |
| 2', 3' | 2.2 | 3", 4" | 1.05 |
| 3', 4' | 9.5 | 4", 5" | 8.09 |
| 4', 5' | 9.2 | 5", 6"a | 5.76 |
| 5', 6' | 6.0 | 5", 6"b | 3.61 |
| | | 6"a, 6"b | -10.86 |
| | | 4", 6"a | -0.1 |

The presented results confirm the conformation of the fructosyl fragment of the N-methyl-N-D-fructosylamphotericin B methyl ester presented by formula 4. Other N-methyl-N-glycosyl derivatives of methyl esters of antibiotics of polyene macrolide group were characterized by methods similar to those described above.

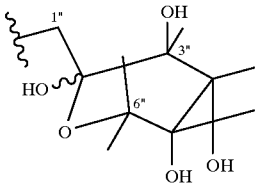

Formula 4

The invention will now be described by reference to the following non-limiting examples. Further embodiments falling within the scope of the invention will be apparent to a skilled person.

Anti-Fungal Activity

For all of the prepared compounds antifungal activity and also toxicity in vitro were determined. For the compound with the best properties, that means for the N-methyl-N-D-fructosylamphotericin B methyl ester aspartate, activity and toxicity in vivo were also determined.

In Vitro Antifungal Activity

The antifungal activity of compounds was determined following the standard for polyene macrolide procedure. The liquid Sabouraud medium was inoculated with 10⁴ cells/ml of test organism *Candida albicans* ATCC 262778 and incubated for 24 hours at 30° C. with the tested antibiotic (serial dilutions). Amphotericin B was used as the reference. Compounds were dissolved in DMF and suitable amounts of the solutions were added to the medium. Turbidimetric method (660 nm) was applied to determine the degree of growth inhibition. The concentration of antibiotic at which the growth of fungi was inhibited by 50% was determined from the dose response curve. The obtained $IC_{50}$ value characterized antifungal activity of the compound.

In Vitro Toxicity

Toxicity of compounds in vitro against animal cells was determined using standard for polyene macrolides procedure, by the determination of the degree of haemolysis of human erythrocytes. Human erythrocytes isolated from fresh, citrated human blood were washed twice with cold saline. The cells were diluted 250 times with saline and equilibrated for 30 minutes at 37° C. Samples of erythrocytes were incubated with various concentrations of antibiotics (the base solution in DMF) for 30 minutes at 37° C. After centrifugation the lysis of erythrocytes was assessed by determination of the haemoglobin released to the solution. Optical density of the supernatant was measured at 550 ppm. The results were expressed by $EH_{50}$ value, as concentration of antibiotic at which 50% of hemolysis occurred. The values of $EH_{50}$ were read from a curve relating the degree of hemolysis with antibiotic dose.

In Vivo Toxicity

In vivo toxicity was determined for methyl ester of N-methyl-N-D-fructosylamphotericin B L-aspartate as the maximum tolerated dose (MTD), and as the acute toxicity ($LD_{50}$). To determine MTD dose the compound was dissolved in 5% solution of glucose, and administered intravenously and intraperitonealy to Balb/c mice in single and multiple doses. The maximum single tolerated dose was 100 mg/kg for the intravenous and more than 200 mg/kg for the intraperitoneal administration. The maximum multiple tolerated dose for intraperitoneal administration of 100 mg/kg for 5 days was much higher. For such dose, toxic effects were not observed during 20 days of observation.

The acute toxicity, $LD_{50}$ of methyl ester of N-methyl-N-D-fructosylamphotericin B L-aspartate was determined for Swiss Webster female mice of average weight of 20 g. Various doses of the tested compound, and for comparison, amphotericin B in form of Fungizone, dissolved in 5% glucose were given intravenously to the animals. The administered volume of the solution was 0.5 ml. 0.5 ml of 5% solution of glucose was administered to mice as a control. Every dose of both preparations was administered to 5 mice. The animals were observed for 7 days. Next, the animals were killed, and some serum indexes were determined. No increased level of aspartate aminotransferase or creatinine were found in comparison with the control. For methyl ester of N-methyl-N-D-fructosylamphotericin B L-aspartate, the $LD_{50}$ was found to be 400 mg/kg, while for amphotericin B in form of Fungizone it was 6 mg/kg.

Chemotherapeutic Efficacy

Chemotherapeutic efficacy of methyl ester of N-methyl-N-D-fructosylamphotericin B L-aspartate was determined using systemic murine candidose model. *Candida albicans* was grown overnight in Sabouraud dextrose broth at room temperature. The fungal cells were centrifuged, washed twice with 0.9% solution of sodium chloride, and suspended in physiological salt solution. Female Swiss Webster mice of 25 g weight, were injected intravenously with $10^5$ cells of Candida in 0.2 ml of 0.9% sodium chloride solution. Initially, the infection was systemic, but by 2 to 3 days it was localized to the kidneys. Untreated animals usually died between 7 to 14 days post-infection. Three days post-infection, animals were treated intravenously, twice a day, for 5 consecutive days with a 5 to 6 hours interval. Preparation was administered as a solution in 5% glucose. The animals were observed for 5 weeks starting from the day of infection. After this time, the surviving animals were sacrificed, their kidneys were removed, homogenized in sterile water, and the homogenate was placed on Sabouraud dextrose agar, and the grown colonies of Candida were counted. The chemotherapeutic effectiveness was represented as a dose of mg/kg, which in the above test resulted in a survival of 50% of animals, and on clearance of Candida from kidneys of half of the mice. The dose, called $ED_{50}$, was calculated using a method given in J.Hyg. 27,493, (1938). The values of $ED_{50}$ for methyl ester of N-methyl-N-D-fructosylamphotericin B L-aspartate are 2.3 mg/kg based on the survival, and 6 mg/kg based on the kidneys clearance.

PREPARATION EXAMPLES

N-Methyl-N-glycosyl derivatives of methyl esters of antibiotics of polyene macrolide group, their salts, and methods of preparation are illustrated by the examples given below.

Example I 1 g of amphotericin B ($E^{1\%}_{1cm}$=1350 at 382 nm, MeOH) was dissolved in 15 ml of N,N-dimethylformamide, 0.3 g of D-glucose was added, and the mixture was stirred in darkness at 37° C. for 40 hours. Next the reaction was cooled and a solid was precipitated with an excess of diethyl ether. The solid was centrifuged, washed twice with diethyl ether and dried under reduced pressure. To remove an excess of glucose the solid was suspended in 20 ml of water, centrifuged, washed twice with small amount of water, twice with acetone, and next twice with diethyl ether. The product was dried under reduced pressure to give 0.98 g of N-D-Fructosylamphotericin B ($E^{1\%}_{1cm}$=1200 at 382 nm, MeOH). The product was dissolved, with stirring, in 10 ml of N,N-dimethylformamide and 50 ml of diethyl ether was added to the solution, to give a fine suspension. The suspension was cooled in ice to 0–2° C., and freshly prepared diethyl ether solution of 2.5 mole of diazomethane per 1 mole of N-D-fructosylamphotericin B, was added with vigorous stirring. The reaction was followed by thin layer chromatography on silica gel in chloroform-methanol-water 10:6:1 v/v solvent system. After completion of the reaction, what took about 2 hours, the excess of diazomethane and diethyl ether was evaporated under reduced pressure at temperature not higher than 40° C. The crude product was precipitated from the residue with an excess of diethyl ether, centrifuged, washed twice with diethyl ether, next with n-hexane, and dried under reduced pressure to give 0.95 g of the crude product. Pure N-methyl-D-fructosylamphotericin B methyl ether was isolated from the crude product by column chromatography on Merck Silicagel 60, 70-230 mesh in chloroform-methanol-water 20:8:1 v/v solvent system. Thus, 0.95 g of the crude product was suspended in the mixture of solvents specified above, and if the product dissolved with difficulties, proportions of the same solvents were changed to 10:6:1. The undissolved part was centrifuged off, and the supernatant charged on chromatography column, next developed in the solvent mixture listed above, but in proportion 20:8:1 v/v. The eluate was analysed on silica plates using chloroform-methanol-water 10:6:1 v/v solvent system. The plates were visualized with serium sulphate reagent. Fractions of $R_f$=0.5–0.54 containing pure N-methyl-N-D-fructosyl derivative of amphotericin B methyl ester were collected. The combined fractions were evaporated under reduced pressure. The dry residue was dissolved in small amount of N,N-dimethylformamide, and the product was precipitated with an excess of diethyl ether, the solid was centrifuged, washed twice with diethyl ether and dried in a vacuum desiccator. 0.137 g of N-methyl-N-D-fructosylamphotericin B methyl ester, $E^{1\%}_{1cm}$=1300 on 382 nm in methanol, was obtained. The proof of structure was given above in the descriptive part. Antifungal activity of the compound against *Candida albicans*, determined as it was described above, gave $IC_{50}$=0.12 μg/ml, and toxicity for human erythrocytes, determined as described above gave $EH_{50}$ value higher than 350 μg/ml. For comparison, $EH_50$ value for the starting amphotericin B was 1.5 μg/ml. An exact value of $EH_{50}$ for N-methyl-N-D-fructosylamphotericin B methyl ester could not be determined, as above 350 μg/ml the compound was insoluble under conditions of the experiment.

Example II 0.5 g of candidin ($E^{1\%}_{1cm}$=1175 at 382 nm, MeOH) and 0.15 g of D-glucose were dissolved in 10 ml of N,N-dimethylformamide and stirred at 37° C. for 36 hours. Further procedure was analogous to this of the Example I, and resulted in 0.43 g of N-D-fructosylcandidin, $E^{1\%}_{1cm}$=1100 at 382 nm in MeOH. The product was methylated with diazomethane in diethyl ether, analogously as in the Example I to give 0.4 g of crude product. Pure N-methyl-N-D-fructosylcandidin methyl ester was isolated by column chromatography, by method similar to that given in the Example I. Fractions containing pure derivative were characterized on thin layer chromatography by $R_f$=0.49–0.52. The fractions were combined, evaporated to dryness, dissolved in small amount of N,N-dimethylformamide, and solid was precipitated with diethyl ether. The solid was centrifuged, washed with diethyl ether and dried in vacuum desiccator to give 0.05 g of N-methyl-N-D-fructosylcandidin methyl ester; $E^{1\%}_{1cm}$=1200 at 382 nm, in MeOH, $IC_{50}$=0.75 μg/ml and $EH_50$ above 300 μg/ml. Structure of the compound was determined by the same methods as for of N-methyl-N-D-fructosylamphotericin methyl ester.

Example III 2 g of nystatin ($E^{1\%}_{1cm}$=870 at 304 nm, in MeOH) and 0.6 g of D-glucose were dissolved in 35 ml of N,N-dimethylacetamide and stirred at 37° C. for 40 hours. After completion of the reaction the crude product was precipitated with diethyl ether, centrifuged, and dried under vacuum. Then, an excess of glucose was washed off with small amount of water-acetone 1:1 mixture, next with acetone, diethyl ether, and the product was centrifuged and dried in vacuum desiccator to give 1.2 g of N-D-fructosylnystatin ($E^{1\%}_{1cm}$=720 at 304 nm, in MeOH). The product was methylated using diazomethane as in the Example I to give 1.25 g of crude product. The product was purified on silica gel column as in Example I. Fractions containing pure N-methyl-N-D-fructosylnystatin methyl ester were characterized on thin layer chromatography by $R_f$=0.49–0.52 as in the Example I. The fractions were combined, evaporated to dryness at 30° C. under reduced pressure, dissolved in small amount of N,N-dimethylformamide, and product was precipitated with diethyl ether. The product was centrifuged, washed with diethyl ether and dried in vacuum desiccator to give 0.17 g of N-methyl-N-D-fructosylnystatin methyl ester, $E^{1\%}_{1cm}$≈900 at 304 nm, in MeOH. Structure of the compound was determined by a method described for N-methyl-N-D-fructosylamphotericin B methyl ester. For the obtained compound $IC_{50}$32 6.8 μg/ml and $EH_50$ above 300 μg/ml were found.

Example IV 0.79 g of vacidin, the main component of antibiotic complex aurofacin, ($E^{1\%}_{1cm}$≈900 at 378 nm, in MeOH) and 0.22 g of D-glucose in 15 ml of N,N-dimethylacetamide were stirred at 37° C. for 18 hours. After completion of the reaction mixture was cooled and solid was precipitated with an excess of diethyl ether. The solid was centrifuged, washed with diethyl ether and dried under reduced pressure to give 0.8 g of crude N-D-fructosylvacidin ($E^{1\%}_{1cm}$=720 at 378 nm, in MeOH). The obtained derivative was methylated using diazomethane, as in Example I to give 0.5 g of crude product. Pure N-methyl-N-D-fructosylvacidin methyl ester was isolated by chromatography on silica gel column similarly as it was described in the Example I, but the column was developed with chloroform-methanol-water 30:8:1 solvent system. Fractions containing pure derivative of vacidin and having on thin layer chromatography value of $R_f$=0.53–0.55 in chloroform-methanol-water 13:8:1 solvent system were collected and combined. Further procedure was as in the Example III. 0.07 g of N-methyl-N-D-fructosylvacidin methyl ester was obtained ($E^{1\%}_{1cm}$=900 at 378 nm, in MeOH). The compound exhibited $IC_{50}$=0.01 μg/ml and $EH_50$=170 μg/ml. Structure of the compound was determined by a method described for N-methyl-N-D-fructosylamphotericin B methyl ester.

Example V 0.79 g of candicidin D, the main component of antibiotic complex candicidin, was treated identically as described in the Example IV. 0.1 g of N-methyl-N-D-fructosylcandidin D methyl ester was obtained; ($E^{1\%}_{1cm}$=920 at 378 nm, in MeOH, $R_f$ of the compound in thin layer chromatography, under conditions described in Example IV, was 0.50–0.53. The compound exhibited $IC_{50}$=0.01 μg/ml and $EH_50$≈180 μg/ml. Structure of the compound was determined by a method described for N-methyl-N-D-fructosylamphotericin B methyl ester.

Example VI 0.79 of the main component of antibiotic complex trychomycin was treated identically as it was described in the Example IV. 0.1 g of N-methyl-N-fructosyltrychomycin methyl ester was obtained; ($E^{1\%}_{1cm}$=910 at 378 nm, in MeOH, $R_f$ of the compound in thin layer chromatography, under conditions described in Example IV, was 0.49–0.52. The compound exhibited $IC_{50}$=0.013 μg/ml and $EH_50$≈165 μg/ml. Structure of the compound was determined by a method described for N-methyl-N-D-fructosylamphotericin B methyl ester.

Example VII 0.5 g of amphotericin B($E^{1\%}_{1cm}$=1350 at 382 nm, in MeOH), and 0.15 g of L-glucose in 8 ml of N,N-dimethylformamide was stirred at 37° C. for 40 hours. Subsequent operations were as in the Example I. 0.065 g of N-methyl-N-D-fructosylamphotericin B methyl ester was obtained; ($E^{1\%}_{1cm}$=1280 at 382 nm, in MeOH. The compound exhibited $IC_{50}$=0.42 µg/ml and $EH_50$=above 200 µg/ml. Structure of the compound was determined by a method described for methyl ester of N-methyl-N-D-fructosylamphotericin B.

Example VIII 0.52 g of amphotericin B($E^{1\%}_{1cm}$=1350 at 382 nm, in MeOH), and 0.153 g of D-mannose was dissolved in 10 ml of N,N-dimethylformamide and stirred at 37° C. for 40 hours. Subsequent operations were as in the Example I. Prude derivative was isolated by silica gel column chromatography, in a manner analogous to that of the Example I, fractions having in thin layer chromatography, run according to the method described in the Example I, value of $R_f$=0.53–0.55 were collected. Subsequent operations were as in the Example I, 0.08 g of N-methyl-N-D-fructosylamphotericin B methyl ester was obtained; $E^{1\%}_{1cm}$=1280 at 382 nm, in MeOH. The compound exhibited $IC_{50}$=0.42 µg/ml and $EH_50$=above 200 µg/ml. Structure of the compound was determined by a method described for N-methyl-N-D-fructosylamphotericin B methyl ester.

Example IX 0.5 g of amphotericin B($E^{1\%}_{1cm}$=1350 at 382 nm, in MeOH), and 0.3 g of D-lactose in 12 ml of N,N-dimethylformamide was stirred at 37° C. for two days. Subsequent operations were as in the Example I. Prude derivative was isolated by silica gel column chromatography, in a manner analogous to that of the Example I, fractions having in thin layer chromatography, run according to the method described in the Example I, value of $R_f$=0.25–0.30 were collected. 0.08 g of N-methyl-N-D-fructosylamphotericin B methyl ester was obtained; $E^{1\%}_{1cm}$=1000 at 382 nm, in MeOH. The compound exhibited $IC_{50}$=6.0 µg/ml and $EH_50$ above 200 µg/ml.

Example X 0.5 g of N-methyl-N-D-fructosylamphotericin B methyl ester, prepared according to the Example I, was suspended in 10 ml of water and 0.059 g of aspartic acid dissolved in 2 ml of water was added. The solution of acid was added dropwise, with stirring to effect the solution. The solution was filtered to remove a small amount of residual solid and an excess of acetone was added to the clear filtrate until the whole salt was precipitated. The solid was filtered off or centrifuged, washed twice with acetone, twice with diethyl ether and dried under reduced pressure, 0.5 g of methyl ester of N-methyl-N-D-fructosylamphotericin B L-aspartate, $E^{1\%}_{1cm}$=1100 at 382 nm, in MeOH, was obtained. Thin layer chromatography under conditions as in the Example I gave $R_f$=0.5–0.54. Product was soluble in N,N-dimethylformamide, dimethylsulphoxide and 5% water solution of glucose. It was very well soluble in water. The compound exhibited $IC_{50}$=0.125 µg/ml and $Eh_{50}$ above 350 µg/ml.

We claim:

1. An N-alkyl-N-glycosyl derivative of a polyene macrolide antibiotic of formula 1(a),

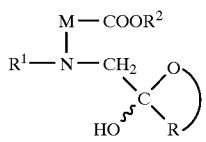

wherein M represents a residue of a polyene macrolide antibiotic, R represents a part of sugar residue formed by reaction of the antibiotic with a mono or oligosaccharide, $R^1$ represents a $C_{1-4}$ alkyl group and $R^2$ represents hydrogen or a $C_{1-4}$ alkyl group.

2. An N-alkyl-N-glycosyl derivative of a polyene macrolide antibiotic of according to claim 1 wherein M is selected from the group consisting of amphotericin B, candidin, candidoin, candidinin, mycoheptin, nystatin, polyfungin, aureofacin, vacidin, trichomycin and candicidin.

3. An N-alkyl-N-glycosyl derivative of a polyene macrolide antibiotic of according to claim 1 wherein R is a part of a sugar residue formed by reaction of the antibiotic with a mono- or oligosaccharide with simultaneous amadori rearrangement.

4. An N-alkyl-N-glycosyl derivative of a polyene macrolide antibiotic of according to claim 1 wherein the mono or oligosaccharide from which the sugar residue R is derived is selected from the group consisting of D-glucose, L-glucose, D-mannose, D-galactose, lactose and maltose.

5. An N-alkyl-N-glycosyl derivative of a polyene macrolide antibiotic of of formula 1(b)

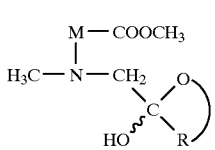

wherein M represents a residue of a polyene macrolide antibiotic and R represents a part of sugar residue formed by reaction of the antibiotic with a mono or oligosaccharide.

6. An N-alkyl-N-glycosyl derivative of a polyene macrolide antibiotic of according to claim 1 wherein $R^2$ is a hydrogen.

7. An N-alkyl-N-glycosyl derivative of a polyene macrolide antibiotic of according to claim 1 wherein $R^2$ is a methyl group.

8. An N-alkyl-N-glycosyl derivative of a polyene macrolide antibiotic of formula 2(a)

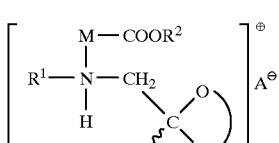

wherein M represents a residue of a polyene macrolide antibiotic, R represents a part of a sugar residue formed by reaction of the antibiotic with a mono or oligosaccharide, $R^1$ represents a $C_{1-4}$ alkyl group and $R^2$ represents hydrogen or a $C_{1-4}$ alkyl group and A represents an anion of an organic or inorganic acid.

9. A salt according to claim 8 wherein M is selected from the group consisting of amphotericin B, candidin, candidoin, candidinin, mycoheptin, nystatin, polyfungin, aureofacin, vacidin, trichomycin and candicidin.

10. A salt according to claim 8 wherein R is a part of a sugar residue formed by reaction of the antibiotic with a mono- or oligosaccharide with simultaneous amadori rearrangement.

11. A salt according to claim 8 wherein the mono- or oligosaccharide from which the sugar residue R is derived is selected from the group consisting of D-glucose, L-glucose, D-mannose, D-galactose, lactose and maltose.

12. A salt of an N-alkyl-N-glycosyl derivative of a polyene macrolide antibiotic of formula 2(b)

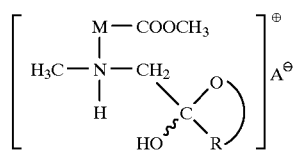

2(b)

wherein M represents a residue of a polyene macrolide antibiotic and R represents a part of a sugar residue formed by reaction of the antibiotic with a mono or oligosaccharide and A represents an anion of an organic or inorganic acid.

13. A salt according to claim 8, wherein $R^2$ is a hydrogen.

14. A salt according to claim 8, wherein $R^2$ is a methyl group.

15. A salt according to claim 8, wherein A is the anion of L-aspartic acid.

16. A method of preparation of an N-alkyl-N-glycosyl derivative of an antibiotic of a polyene macrolide of formula 1(a)

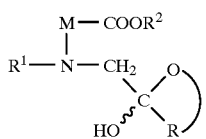

1(a)

wherein M represents a residue of a polyene macrolide antibiotic, R represents a part of a sugar residue formed by reaction of the antibiotic with a mono or oligosaccharide, $R^1$ represents a $C_{1-4}$ alkyl group and $R^2$ represents hydrogen or a $C_{1-4}$ alkyl group, which comprises the steps of reacting a polyene macrolide antibiotic with a mono or oligosaccharide with simultaneous amadori rearrangement, to give the N-glycosyl derivative of the polyene macrolide antibiotic; isolating the amadori rearrangement product; and treating the isolated amadori rearrangement product with an alkylating agent.

17. A method of preparation according to claim 16, wherein the amadori rearrangement product is isolated in the form of a suspension by precipitation from the solution in which the rearrangement occurs.

18. A method of preparation according to claim 16, wherein N,N-dimethylformamide is used to support the amadori rearrangement.

19. A method of preparation according to claim 16, wherein diethyl ether is used to effect formation of a suspension by precipitation of the product of the amadori rearrnagement.

20. A method of preparation according to claim 16, wherein alkylation of the product of the amadori rearrnagement is carried out at reduced temperature.

21. A method of preparation according to claim 20, wherein alkylation is carried out at temperatures of between −5° C. and +5° C.

22. A method of preparation according to claim 16, wherein the alkylating agent is an ethereal solution of diazomethane.

23. A method of preparation compounds of formula 1(a)

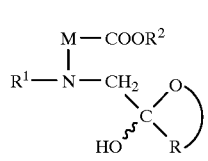

1(a)

wherein M represents a residue of a polyene macrolide antibiotic, R represents a part of a sugar residue formed by reaction of the antibiotic with a mono or oligosaccharide, $R^1$ represents a $C_{1-4}$ alkyl group and $R^2$ represents hydrogen or a $C_{1-4}$ alkyl group, which comprises the steps of forming from a polyene macrolide a first N-protected derivative; reacting said first N-protected derivative with a further protecting group to give a second N-protected-carboxy-protected derivative; alkylating said second derivative to give the N-alkyl N-protected carboxy-protected derivative; removing the N-protecting group and reacting the resulting N-alkyl derivative with a mono-, di- or oligosaccharide, to give, upon simultaneous amadori rearrangement, the N-alkyl-N-glycosyl derivative; removing the carboxy protecting group from said N-alkyl-N-glycosyl derivative and derivatizing said carboxyl group.

24. A method according to claim 23, wherein the N-protecting (amino) group is a trifluoroacetyl group.

25. A method according to claim 24, wherein the N-protecting trifluoroacetyl group is derived from trifluoroacetic anhydride and trifluoroacetic acid.

26. A method according to claim 23, wherein the carboxy protecting groups is a labile ester group.

27. A method according to claim 23, wherein the carboxy protecting group is selected from the group consisting of a benzyl ester, a p-methoxybenzyl ester and a t-butyl ester.

28. A method according to claim 23, wherein the alkylating agent is selected from the group consisting of a dialkyl sulphate and an alkyl iodide.

29. A method according to claim 23, wherein the alkylating agent is selected from the group consisting of dimethyl sulphate and methyl iodide.

30. A method of preparation of a salt of an N-alkyl-N-glycosyl derivative of a polyene macrolide antibiotic of formula 2(a)

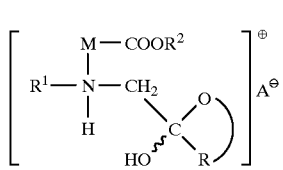

2(a)

wherein M represents a residue of a polyene macrolide antibiotic, R represents a part of a sugar residue formed by reaction of the antibiotic with a mono or oligosaccharide, $R^1$ represents a $C_{1-4}$ alkyl group, $R^2$ represents hydrogen or a $C_{1-4}$ alkyl group, and A represents an anion of an organic or inorganic acid, which comprises the steps of suspending an N-alkyl-N-glycosyl derivative of formula 1(a) according to claim 1 in sufficient water to effect formation of a homogeneous suspension, acidifying the resulting suspension and isolating the product.

31. A method of preparation of a salt of an N-alkyl-N-glycosyl derivative of a polyene macrolide antibiotic according to claim 30 wherein an organic or inorganic acid is used to acidify the suspension.

32. A method of preparation of a salt of an N-alkyl-N-glycosyl derivative of a polyene macrolide antibiotic according to claim 31 wherein L-aspartic acid is used to acidify the suspension.

33. A method for the treatment of a fungal infection in a human or an animal patient which comprises the administration thereto of an N-alkyl-N-glycosyl derivative of formula 1(a) or a salt thereof of formula 2(a),

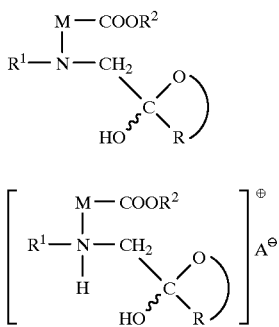

1(a)

2(a)

wherein M represents a residue of a polyene macrolide antibiotic, R represents a part of a sugar residue formed by reaction of the antibiotic with a mono or oligosaccharide, $R^1$ represents a $C_{1-4}$ alkyl group, $R^2$ represents hydrogen or a $C_{1-4}$ alkyl group, and A represents an anion of an organic or inorganic acid.

34. A method according to claim 33 in which the N-alkyl-N-glycosyl derivative of formula 1(a) or 2(a) is administered by perfusion.

35. A composition comprising an N-alkyl-N-glycosyl derivative of formula 1(a) or a salt thereof of formula 2(a),

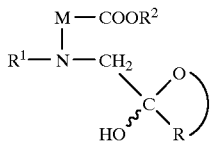

1(a)

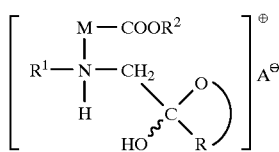

2(a)

wherein M represents a residue of a polyene macrolide antibiotic, R represents a part of a sugar residue formed by reaction of the antibiotic with a mono or oligosaccharide, $R^1$ represents a $C_{1-4}$ alkyl group, $R^2$ represents hydrogen or a $C_{1-4}$ alkyl group, and A represents an anion of an organic or inorganic acid and a physiologically acceptable carrier.

36. A composition according to claim 35, wherein the composition is in the form of a unit dosage form.

37. A composition according to claim 35 comprising an N-methyl-N-glycosyl derivative of formula 1(b) or a salt thereof of formula 2(b)

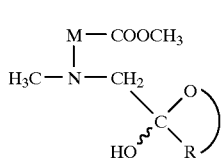

1(b)

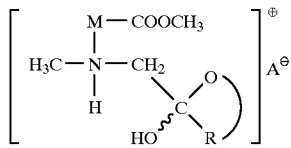

2(b)

wherein M represents a residue of a polyene macrolide antibiotic, R represents a part of a sugar residue formed by reaction of the antibiotic with a mono or oligosaccharide and A represents an anion of an organic or inorganic acid.

38. A composition according to claim 35, which further comprises a known anti-fungal agent.

39. A composition according to claim 35 which is formulated for intravenous, intraperitoneal, oral, topical, subcutaneous, rectal or vaginal administration.

* * * * *